(12) United States Patent
Madabhushi et al.

(10) Patent No.: US 9,595,103 B2
(45) Date of Patent: Mar. 14, 2017

(54) TEXTURAL ANALYSIS OF LUNG NODULES

(71) Applicant: Case Western Reserve University, Cleveland, OH (US)

(72) Inventors: Anant Madabhushi, Shaker Heights, OH (US); Mirabela Rusu, Cleveland, OH (US); Mahdi Orooji, Cleveland, OH (US); Mehdi Alilou, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/873,611

(22) Filed: Oct. 2, 2015

(65) Prior Publication Data

US 2016/0155225 A1    Jun. 2, 2016

Related U.S. Application Data

(60) Provisional application No. 62/085,616, filed on Nov. 30, 2014.

(51) Int. Cl.
| | | |
|---|---|---|
| *G06T 7/00* | (2006.01) | |
| *A61B 6/00* | (2006.01) | |
| *A61B 6/03* | (2006.01) | |

(52) U.S. Cl.
CPC ............ *G06T 7/0012* (2013.01); *A61B 6/032* (2013.01); *A61B 6/50* (2013.01); *A61B 6/5217* (2013.01); *G06T 2200/04* (2013.01); *G06T 2207/10081* (2013.01); *G06T 2207/30064* (2013.01)

(58) Field of Classification Search
USPC ........ 382/100, 103, 106–107, 128–133, 160, 382/162, 173, 181, 190, 199, 219, 232, 382/254, 274, 276, 286–291, 305, 224; 378/1, 4, 21; 600/300
See application file for complete search history.

(56) References Cited

U.S. PATENT DOCUMENTS

| | | | |
|---|---|---|---|
| 2008/0002870 A1* | 1/2008 | Farag .................. | G06K 9/0014 382/128 |
| 2009/0148010 A1* | 6/2009 | Boroczky ............ | G06K 9/3233 382/128 |
| 2009/0252395 A1* | 10/2009 | Chan ..................... | A61B 6/466 382/131 |
| 2010/0111396 A1* | 5/2010 | Boucheron .......... | G06K 9/0014 382/133 |

(Continued)

*Primary Examiner* — Seyed Azarian
(74) *Attorney, Agent, or Firm* — Eschweiler & Potashnik, LLC

(57) ABSTRACT

Methods, apparatus, and other embodiments associated with classifying a region of tissue using textural analysis are described. One example apparatus includes an image acquisition logic that acquires an image of a region of tissue demonstrating GGO nodule pathology, a delineation logic that distinguishes GGO nodule tissue within the image from the background of the image, a texture logic that extracts a set of texture features from the image, a phenotype signature logic that computes a phenotypic signature from the image, a shape logic that extracts a set of shape features from the image, and a classification logic that classifies the GGO nodule tissue based, at least in part, on the set of texture features, the phenotypic signature, or the set of shape features. A prognosis for a patient may be provided based on the classification of the image.

21 Claims, 8 Drawing Sheets

(56) References Cited

U.S. PATENT DOCUMENTS

2011/0075920 A1* 3/2011 Wu ............... G06K 9/4638
382/160
2012/0088981 A1* 4/2012 Liu ............... G06K 9/6215
600/300

* cited by examiner

TEXTURAL ANALYSIS OF LUNG NODULES

CROSS REFERENCE TO RELATED APPLICATIONS

This application claims the benefit of U.S. Provisional Application 62/085,616 filed Nov. 30, 2014.

BACKGROUND

Variations of lung nodule invasiveness and morphology relate to prognosis and patient outcomes. One approach for diagnosing cancer is histopathological examination of biopsy tissue. The examination may produce a diagnostic profile based on attributes including cell morphology, cytoplasmic changes, cell density, and cell distribution. Visual characterization of tumor morphology is, however, time consuming and expensive. Visual characterization is also subjective and thus suffers from inter-rater and intra-rater variability. Conventional visual characterization of lung nodule morphology by a human pathologist may therefore be less than optimal in clinical situations where timely and accurate classification can affect patient outcomes.

Computerized tomography (CT) is used to image nodules in lungs. Chest CT imagery may be used to detect and diagnose non-small cell lung cancer. However, conventional approaches have been challenged when defining radiographic characteristics that reliably describe the degree of invasion of early non-small cell lung cancers with ground glass opacity (GGO). For example, conventional CT imagery based approaches may find it difficult, if even possible at all, to reliably discriminate nodules caused by benign fungal infections from non-small cell lung cancer nodules.

The degree of invasion of a lung nodule is correlated with prognosis. For example, patients suffering from minimally invasive nodules may have higher disease free survival rate at five years compared to patients with nodules demonstrating frank invasion. Since radiologists may be challenged to reliably distinguish the level of invasiveness of lung nodules in situ using conventional CT approaches in clinically optimal or relevant time frames, invasive procedures that may be performed that ultimately result in a negative diagnosis. These invasive procedures take time, cost money, and put a patient at additional risk.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
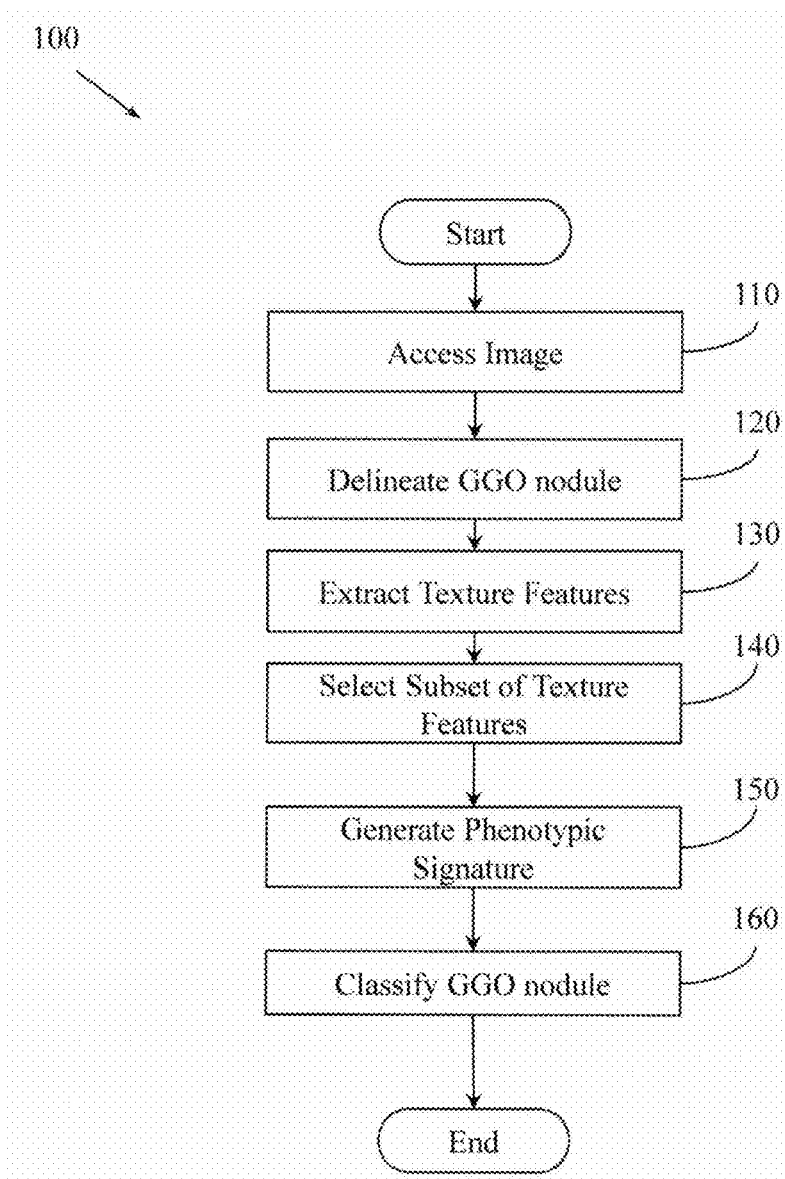
FIG. 1 illustrates an example method of characterizing a GGO nodule in a region of lung tissue.

Variations in tumor invasiveness and morphology may be related to patient prognosis and outcome. In particular, a GGO nodule's level of invasion is strongly correlated to patient prognosis. Conventional methods of diagnosing cancer include visual histopathological examination of a biopsy to create a diagnostic profile based on variations in tumor morphology. However, invasive biopsy may not always be a convenient or appropriate method for assessing GGO nodules. Invasive biopsies cost money, take time, and put a patient at additional risk. A non-invasive approach that provided improved accuracy compared to conventional CT based approaches would reduce the number of unnecessary interventions, reduce the dependency on repetitive or higher resolution CT exams, offer a non-invasive means of assessing response to targeted therapies, and improve patient outcomes. Thus, a timely, non-invasive procedure that results in more accurate discrimination between minimally invasive and frank invasive nodules would offer reduced risk to patients while providing economic benefits to the health care system.

CT imagery is conventionally used to differentiate malignant GGO nodules from other, non-cancerous GGO nodules. Conventional methods of visually assessing GGO nodule invasiveness based on CT imagery are subjective and yield intra and inter-reviewer variability. In one example, of a group of baseline CT chest scans, 51% were found positive for lung nodules. However, only 12% of those lung nodules were found to be malignant. The remainder were determined to be granulomas due to a prior histoplasmosis infection. Conventional CT approaches may focus exclusively on detection of lung nodules, or exclusively on diagnosing malignancy via CT scans. Example apparatus and methods discriminate granulomas caused by fungal infection from carcinomas. Distinguishing fungal infection from carcinoma facilitates reducing surgical interventions that ultimately result in a diagnosis of histoplasmosis.

Example methods and apparatus more accurately distinguish malignant GGO nodules from benign nodules. Since a more accurate distinction is made, example apparatus and methods thus predict patient outcomes in a more consistent and reproducible manner. Example methods and apparatus predict patient outcomes more accurately than conventional methods by employing computerized textural and morphologic analysis of lung CT imagery to distinguish granulomas due to fungal infection from malignant tumors. A GGO nodule may be segmented from an image background. Features may be automatically extracted from the segmented GGO nodule image. Example methods and apparatus may extract texture features and shape features from the GGO nodule image. Example methods and apparatus may also extract tortuosity features from the GGO nodule image. Malignant lung tumors may induce irregular changes to vessel shapes. Example methods and apparatus detect and quantify vessel tortuosity abnormalities on a tumor neighborhood. A subset of extracted features may be selected using principal component analysis (PCA) and then a classification of the GGO nodule image may be generated using linear discriminant analysis (LDA) or quadratic discriminant analysis (QDA).

Figure 6:
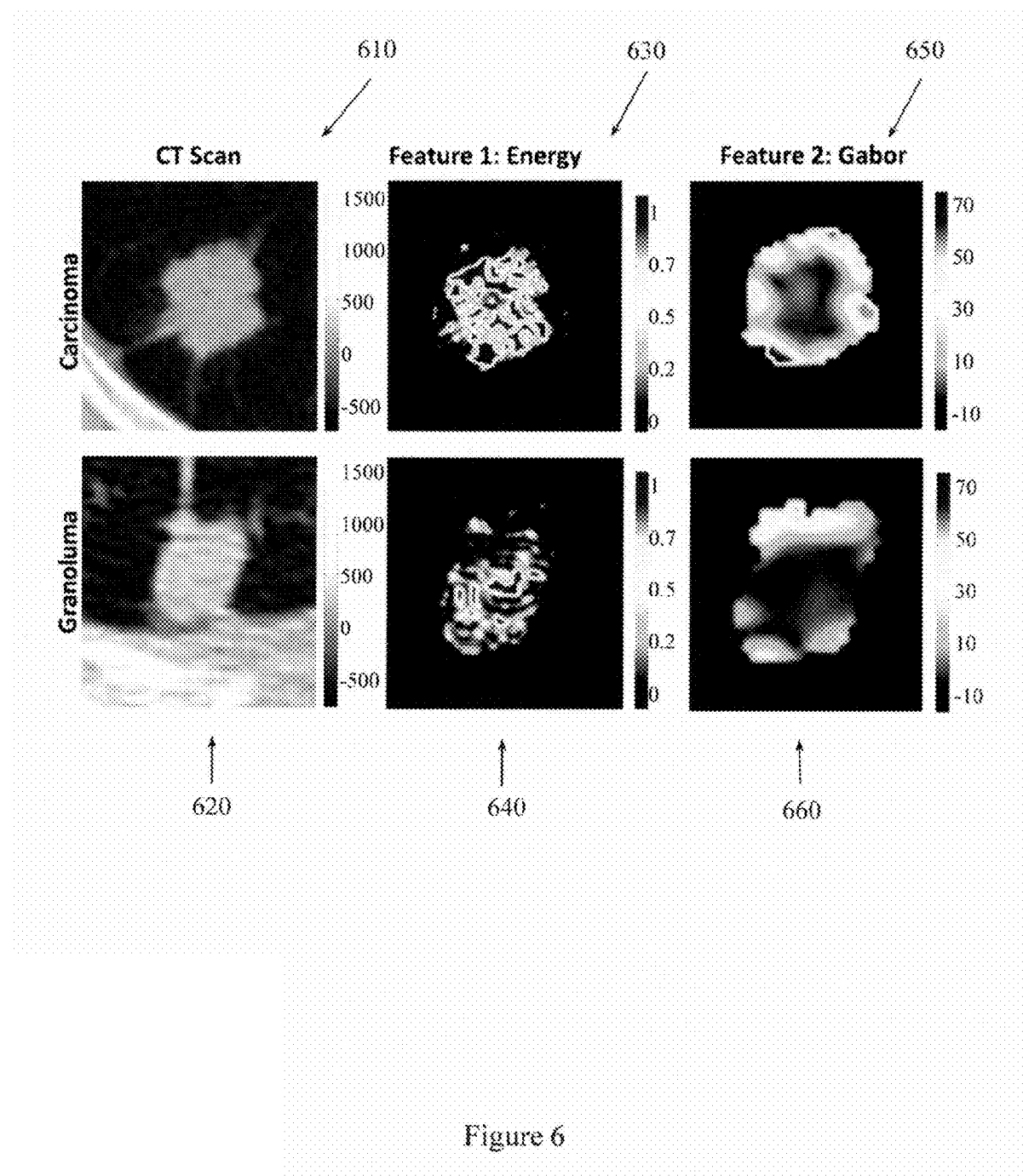
FIG. 6 illustrates textural features of a CT image of a granuloma and a carcinoma.

Carcinomas may have a more chaotic cellular architecture than granuloma. The chaotic cellular architecture may be correlated to an energy feature in an image. The energy feature may be represented as a texture feature or a shape feature. In some embodiments, the energy feature is more pronounced in a CT heatmap of a cancerous GGO nodule than in a CT heatmap of a granuloma because of the more chaotic cellular architecture of the cancerous GGO nodule. FIG. 6 illustrates this property of cancerous GGO nodules compared with granuloma GGO nodules that were caused by benign fungal infections. The chaotic cellular architecture may also be correlated to tortuosity features of vessels associated with a tumor or a GGO nodule.

FIG. 6 illustrates, at 610, a CT scan image of a cancerous GGO nodule identified as a carcinoma. FIG. 6 also illustrates, at 620, a CT scan image of GGO nodule identified as a granuloma. FIG. 6 illustrates, at 630, an energy textural feature extracted from intensity values of image 610 of the cancerous GGO nodule. The energy of a textural feature measures local homogeneity within the image, illustrating how uniform the texture is. FIG. 6 also illustrates a textural feature image 640 of the energy extracted from the image of the benign granuloma 620. The energy feature image 630 of the cancerous GGO nodule displays a more pronounced energy feature than the benign granuloma texture feature image 640, which demonstrates the more chaotic cellular architecture of a cancerous GGO nodule. FIG. 6 also illustrates, at 650, a heatmap of a Gabor feature of the cancerous GGO nodule. The Gabor feature represents texture using a sinusoidal plane wave modulated Gaussian kernel function. FIG. 6 further illustrates, at 660, a heatmap of a Gabor texture feature of the benign granuloma.

Example methods and apparatus may also employ 3-fold cross validation where N=46 for training a classifier and N=16 for testing a classifier. Example methods and apparatus may train a classifier or test a classifier with other, different numbers of subjects. For example, a human pathologist may manually delineate and classify one hundred GGO nodules for a training set and thirty nodules for a testing set. Example methods and apparatus may classify the GGO nodule image as a carcinoma, adenocarcinoma, or as a granuloma. Example methods and apparatus may also classify the GGO nodule image as non-invasive, minimally invasive, or frank invasive. Other classifications may be employed.

Example methods and apparatus thus improve on conventional methods by more accurately distinguishing between pathological and benign lung nodules.

Example methods and apparatus distinguish granuloma from carcinoma with an accuracy of at least 92% area under the curve (AUC) when using texture features and shape features with a linear discriminant analysis (LDA) classifier. Example methods and apparatus distinguish frank invasive GGO nodules from non-invasive or minimally invasive GGO nodules with an accuracy of at least 78% AUC when using three texture features selected by PCA with a quadratic discriminant analysis (QDA) classifier. In contrast, conventional approaches using just Laws feature achieve accuracies of approximately 0.61 AUC, while conventional approaches using just Gabor features achieve accuracies of approximately 0.68 AUC. In these examples, a minimally invasive GGO nodule is defined as a GGO nodule with 5 mm or less invasion, and a frank invasive GGO nodule is defined as a GGO nodule with more than 5 mm invasion. In other embodiments, minimally invasive GGO nodules and frank invasive GGO nodules may be defined on other dimensions.

By increasing the accuracy with which malignant GGO nodules are distinguished from benign lung GGO nodules, example methods and apparatus produce the concrete, real-world technical effect of reducing the time required to evaluate medical imagery while increasing the accuracy of the evaluation. Additionally, example apparatus and methods increase the probability that at-risk patients receive timely treatment tailored to the particular pathology they exhibit. Example methods and apparatus may also reduce the number of invasive procedures needed to accurately characterize GGO nodules. The additional technical effect of reducing the expenditure of resources and time on patients who are less likely to suffer recurrence or disease progression is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates an example computerized method 100 for characterizing a GGO nodule in a region of lung tissue. Method 100 includes, at 110, accessing an image of a region of lung tissue. Accessing the image may include accessing a CT image of the region of lung tissue. The CT image may be stored, for example, in a computer memory or may be provided across a computer network. In one embodiment, the CT image is a 1 mm to 5 mm thick, no-contrast chest CT image. In another embodiment, other images sizes or other imaging techniques may be employed.

Method 100 also includes, at 120, delineating a GGO nodule in the image. The GGO nodule may be automatically delineated by distinguishing GGO nodule tissue within the image from the background of the image. The GGO nodule tissue may be automatically distinguished using threshold based segmentation, deformable boundary models, active-appearance models, active shape models, graph based models including Markov random fields (MRF), min-max cut approaches, or other image segmentation approaches.

Method 100 also includes, at 130, extracting a set of texture features from the image of the GGO nodule. The set of texture features includes a gray-level statistical feature, a steerable Gabor feature, a Haralick feature, a Law feature, a Law-Laplacian feature, a local binary pattern (LBP) feature, inertia, a correlation feature, a difference entropy feature, a contrast inverse moment feature, or a contrast variance feature. In one embodiment, the set of texture features includes at least sixty three texture features. In another embodiment, the set of texture features includes at least one hundred texture features. For example, a set of one hundred texture features may include 13 Haralick features, 4 gray features, 13 gradient features, 19 Gabor features, 1 LBP feature, 25 Law features, or 25 Law-Laplacian features. In other embodiments, other numbers or types of texture features may be extracted.

Method 100 also includes, at 140, selecting a subset of texture features from the set of texture features. In one embodiment, the subset of texture features is selected by reducing the set of texture features using a PCA. The PCA of the set of texture features selects a subset of texture features from the set of texture features. The subset of texture features achieves a threshold level of discriminability. For example, the PCA may select one energy feature and one Gabor feature that are the most discriminative, based on a particular set of CT images, for distinguishing carcinoma from granuloma. The subset of texture features may include as few as two texture features. The level of discriminability may be user adjustable. For example, in a first clinical situation, a subset of texture features that achieves 0.8 AUC accuracy in distinguishing carcinoma from granuloma may be acceptable. A feature may be considered to have a desirable level of discriminability when the means of two separate classes are more than a threshold distance from each other, and where the variance of a class is less than a threshold distance, in comparison to the distance between the means. In one embodiment, the Fisher criterion, which is the squared difference of the means divided by the sum of the variances, may be used to quantitatively establish a desirable level of discriminability.

Figure 7:
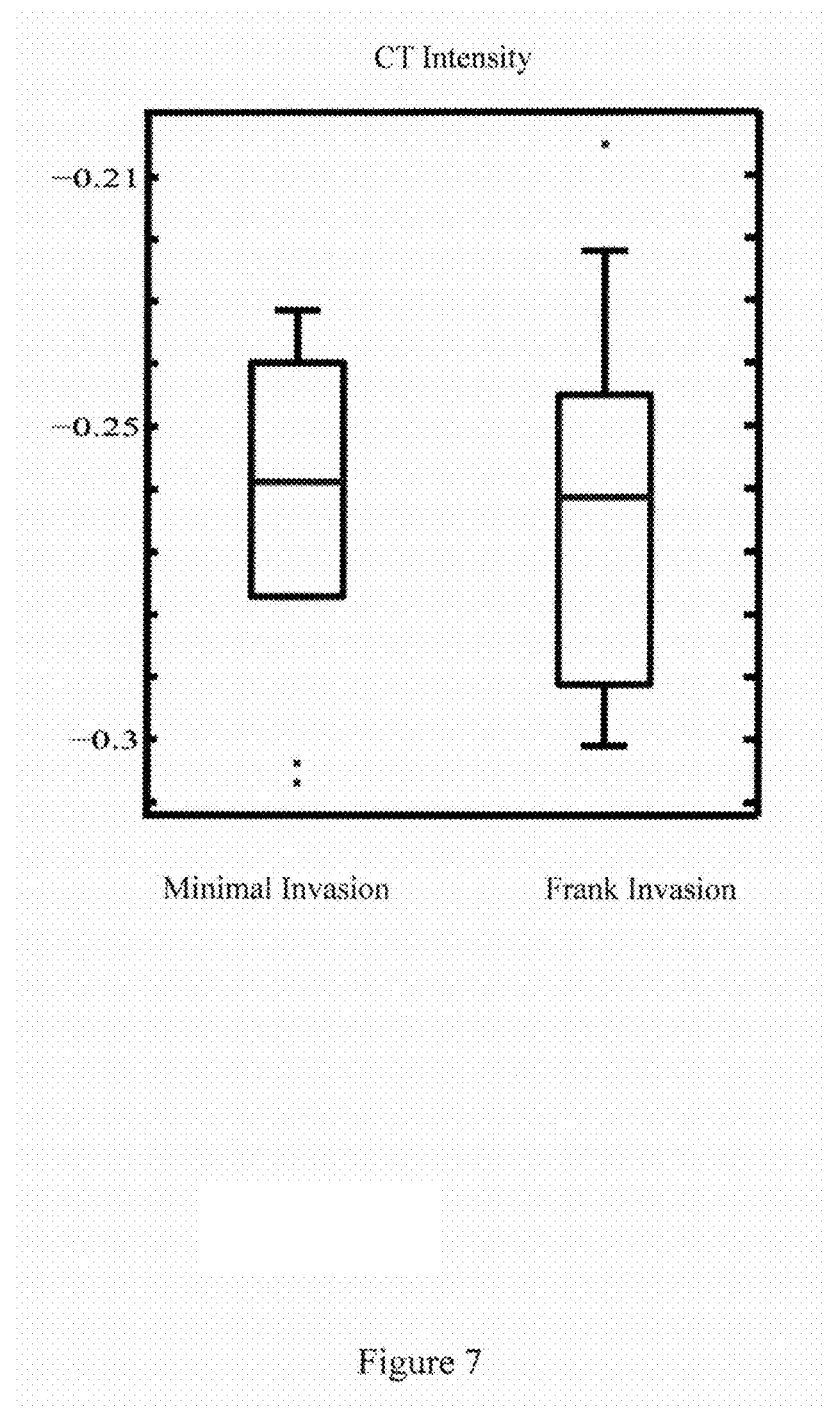
FIG. 7 is a boxplot of CT intensities of a CT image of a minimally invasive GGO nodule and a frank invasive GGO nodule.

FIG. 7 is a boxplot of CT intensities of a CT image of a minimally invasive GGO nodule and a frank invasive GGO nodule. In FIG. 7, the Y-axis indicates the normalized value of the average Hounsfield unit within a nodule in the CT image. FIG. 7 illustrates the challenge involved with classifying GGO nodules using conventional CT imagery approaches. FIG. 7 demonstrates that the CT intensities of a minimally invasive GGO nodule and frank invasive GGO nodule overlap significantly. In this example, the median of the CT intensity for the minimally invasive GGO nodule is within a threshold distance from the median of the frank invasive GGO. Thus, an attempt to classify a GGO nodule based on just CT intensity is unlikely to be acceptably accurate.

Figure 8:
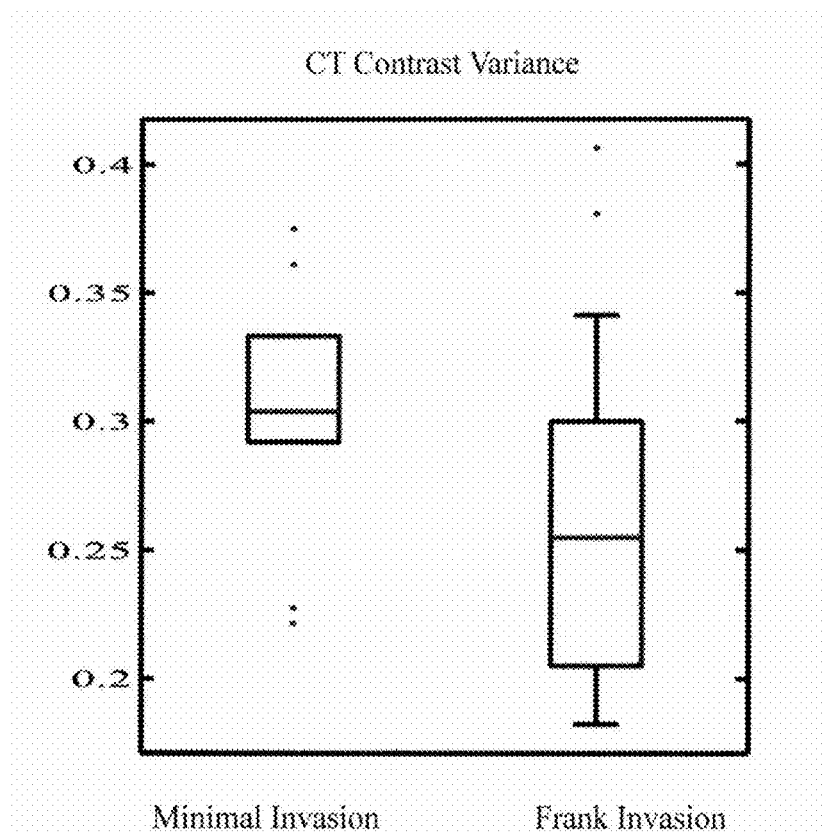
FIG. 8 is a boxplot of CT contrast variance of a CT image of minimally invasive GGO nodule and frank invasive GGO nodule.

FIG. 8 is a boxplot of CT contrast variance of a CT image of a minimally invasive GGO nodule and a frank invasive GGO nodule. In FIG. 8, the Y-axis indicates the normalized value of the average Hounsfield unit with a nodule in the CT image. FIG. 8 demonstrates how texture features, like contrast variance, may have a more desirable level of discriminability. In this example, the median of the CT contrast variance for the minimally invasive GGO nodule is more than a threshold distance from the median of the CT contrast variance for the frank invasive GGO.

Method 100 also includes, at 150, generating a phenotypic signature for the nodule. In one embodiment, the phenotypic signature is generated using Fisher criteria ranking. In another embodiment, the phenotypic signature is generated using other techniques.

Method 100 also includes, at 160, controlling a computer aided diagnosis (CADx) system to generate a classification of the GGO nodule in the image. The classification may be based, at least in part, on the subset of texture features or the phenotypic signature. In one embodiment, the CADx system generates the classification of the image of the GGO nodule using a QDA classifier. In another embodiment, the CADx system may generate the classification using other, different types of classifier. The classifier may be trained and tested on a set of images of pre-classified GGO nodules. In one embodiment, the image is of a region of tissue demonstrating adenocarcinoma pathology. Controlling the CADx system to generate the classification of the GGO nodule based, at least in part, on the subset of texture features and the phenotypic signature, includes classifying the image of the GGO nodule as frank invasive adenocarcinoma or minimally invasive adenocarcinoma.

Example methods and apparatus facilitate more accurate characterization of GGO nodules found in CT images than conventional approaches. Example methods and apparatus thus improve on conventional methods by characterizing GGO nodules as frank invasive, non-invasive, or minimally invasive, or as carcinomas, adenocarcinomas, or granulomas with greater accuracy and with less subjective variability than conventional methods. Example methods and apparatus therefore facilitate more judicious application of biopsies and surgical resection in a population undergoing CT screening for lung cancer.

Using a more appropriately determined and applied treatment may lead to less therapeutics being required for a patient or may lead to avoiding or delaying a biopsy, a resection, or other invasive procedure. When regions of cancerous tissue, including GGO nodules detected in CT scans, are more quickly and more accurately classified, patients with poorer prognoses may receive a higher proportion of scarce resources (e.g., therapeutics, physician time and attention, hospital beds) while those with better prognoses may be spared unnecessary treatment, which in turn spares unnecessary expenditures and resource consumption. Example methods and apparatus may thus have the real-world, quantifiable effect of improving patient outcomes.

While FIG. 1 illustrates various actions occurring in serial, it is to be appreciated that various actions illustrated in FIG. 1 could occur substantially in parallel. By way of illustration, a first process could delineate a GGO nodule in a CT image, a second process could extract texture features from the CT image, and a third process could extract shape features from the CT image. While three processes are described, it is to be appreciated that a greater or lesser number of processes could be employed and that lightweight processes, regular processes, threads, and other approaches could be employed.

Figure 2:
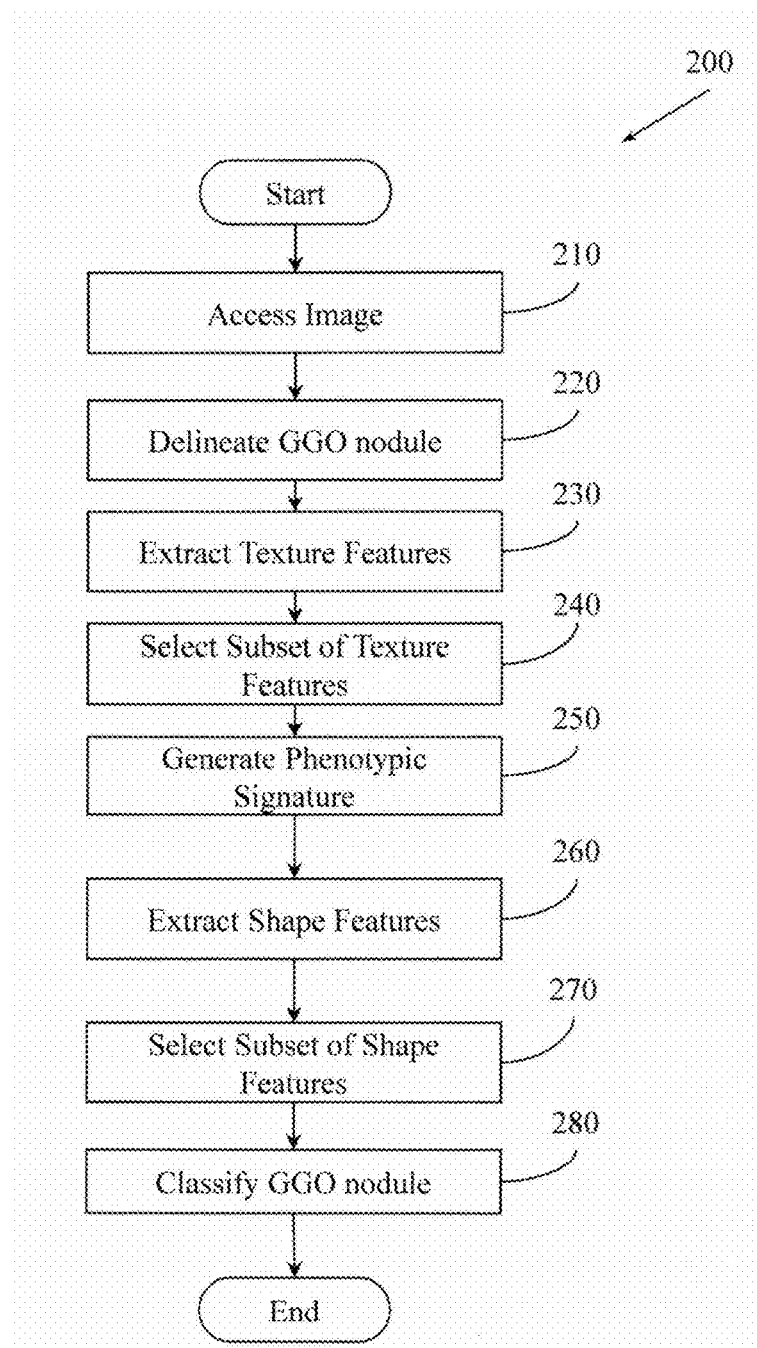
FIG. 2 illustrates an example method of characterizing a GGO nodule in a region of lung tissue.

FIG. 2 illustrates an example method 200 for characterizing a GGO nodule in a region of lung tissue. Method 200 is similar to method 100 but includes additional actions. Method 200 includes actions 210, 220, 230, 240, and 250 which are similar to actions 110, 120, 130, 140, and 150 described above with respect to method 100.

Method 200 also includes, at 260, extracting a set of shape features from the image of the GGO nodule. The set of shape features includes a location feature, a size feature, a width feature, a height feature, a depth feature, a perimeter feature, an eccentricity feature, an eccentricity standard deviation, a compactness feature, a roughness feature, an elongation feature, a convexity feature, an extend feature, an equivalent diameter feature, or a sphericity feature. The location feature describes the spatial information of a pixel in the image of the GGO nodule, the size feature describes the number of pixels within the segmented image of the GGO nodule, and the perimeter feature describes the distance around the boundary of the segmented GGO nodule. The eccentricity feature describes the eccentricity of an ellipse that has the same second moments as the nodule. The compactness feature describes the isoperimetric quotient of the nodule. The roughness feature describes the perimeter of a lesion in a slice of the image of the GGO nodule divided by the convex perimeter of the lesion. The elongation feature describes the ratio of minor axis to the major axis of the image of the GGO nodule, and the convexity feature describes the ratio of a tumor image slice to the convex hull of the tumor. The extend feature describes the ratio of pixels in the tumor region to pixels in the total bounding box. The equivalent diameter feature describes the diameter of a circle having the same area as a tumor image slice, and the sphericity feature describes the three-dimensional compactness of the nodule. In one embodiment the set of shape features includes at least twenty-five shape features. In another embodiment, the set of shape features may include other numbers of shape features, or other, different shape features. A feature may be calculated in three dimensional (3D) space, or in two dimensional (2D) space. For example, width, height, depth, or sphericity features may be calculated in 3D space.

Method 200 also includes, at 270, selecting a subset of shape features from the set of shape features. In one embodiment, the subset of shape features includes eccentricity, eccentricity standard deviation, or elongation features. In another embodiment, the subset of shape features may include other, different shape features. The subset of shape features may be selected from the set of shape features using PCA.

Method 200 also includes, at 280, controlling the CADx system to generate the classification of the image of the GGO nodule as a carcinoma or a granuloma. The classification may be based, at least in part, on the subset of texture features and the subset of shape features. Basing the classification on both the subset of texture features and the subset of shape features improves on conventional approaches by increasing the accuracy with which the image of the GGO may be classified. In one embodiment, the CADx system generates the classification of the image of the GGO nodule using a LDA classifier or a QDA classifier. In one embodiment, an LDA classifier using a median textural feature and eccentricity standard deviation shape feature achieves an accuracy of at least 0.92 AUC. The LDA classifier or the QDA classifier may be trained and tested on a set of GGO images pre-classified as carcinoma or granuloma.

In one embodiment, method 200 may also automatically segment vessels associated with the nodule. Method 200 may identify a centerline of a vessel and branching points associated with the vessel. Method 200 calculates the torsion for a vessel segment using a distance metric. The torsion of a vessel segment is defined as 1−(Distance/Length) where distance is the Euclidean distance of the start and end point of the segment, and where length is the number of voxels along the vessel segment. Method 200 also extracts the curvature of a vessel segment. Curvature at a voxel of a vessel segment is proportional to the inverse of an osculating circle's radius. The osculating circle is fitted to a collection of three neighboring points along the centerline of a vessel. For a plurality of points along the center line of a vessel, method 200 fits a circle to compute the curvature of a specific point. Method 200 then computes mean and standard deviation of the curvature for points along the vessel.

Method 200 may then extract a set of tortuosity features from the image of the GGO nodule. The tortuosity features describe vessels associated with the GGO nodule. The set of tortuosity features includes the mean of torsion of a vessel segment, or the standard deviation of torsion of a vessel segment. The set of tortuosity features also includes the mean and standard deviation of the mean curvature of a group of vessel segments. The set of tortuosity features also includes the mean and standard deviation of the standard deviation of a vessel segment curvature and a total vessel segment length. In one embodiment, the set of tortuosity features includes at least seven tortuosity features. In another embodiment, the set of tortuosity features may include other numbers of tortuosity features, or other, different tortuosity features. Method 200 may also select of subset of tortuosity features from the set of tortuosity features. Method 200 may also include controlling the CADx system to generate the classification of the image of the GGO nodule based, at least in part, on the subset of tortuosity features, the subset of texture features and the subset of shape features.

Figure 3:
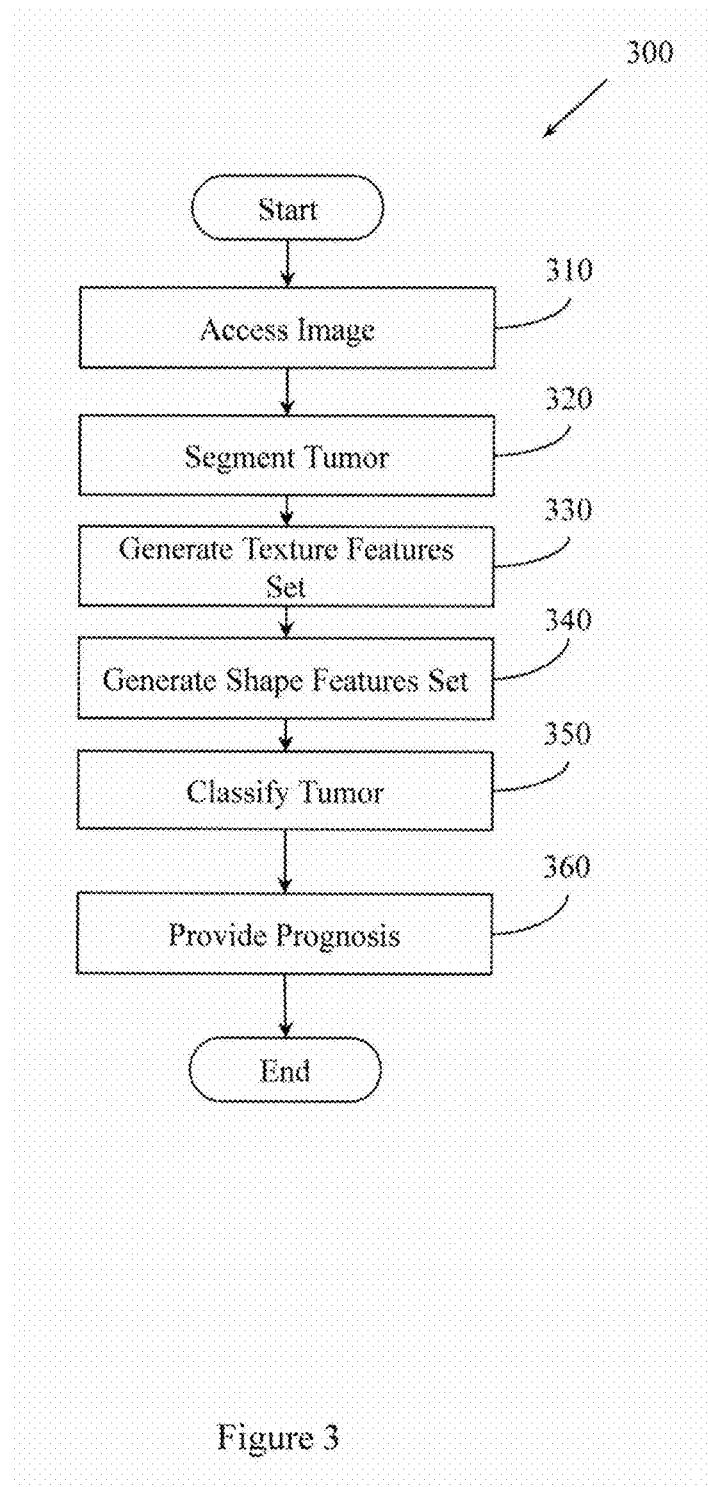
FIG. 3 illustrates an example method of distinguishing invasive tumors from non-invasive tumors in chest CT images.

FIG. 3 illustrates an example method 300 for distinguishing invasive tumors from non-invasive tumors in chest CT images. Method 300 includes, at 310 accessing an image of a region of tissue demonstrating cancerous pathology. In one embodiment, the image is a 1 mm to 5 mm thick, no-contrast chest CT image. In another embodiment, other image types or image dimensions may be used. Accessing the image may include retrieving electronic data from a computer memory, receiving a computer file over a computer network, or other computer or electronic based action.

Method 300 also includes, at 320, segmenting a tumor in the image from the background of the image. Segmenting the tumor in the image from the background of the image involves identifying the portion of the image that represents the tumor to distinguish that portion from the background. In one embodiment, the tumor is automatically segmented from the background of the image. In another embodiment, a human pathologist manually delineates the tumor from the background of the image. In another embodiment, vessels associated with the tumor are also segmented.

Method 300 also includes, at 330, selecting a set of texture features from the segmented image. In one embodiment, the set of texture features may include a gray-level statistical feature, a steerable Gabor feature, a Haralick feature, a Law feature, a Law-Laplacian feature, an LBP feature, an inertia feature, a correlation feature, a difference entropy feature, a contrast inverse moment feature, or a contrast variance feature. In another embodiment, other, different texture features may be selected. The inertia feature describes the contrast or local intensity variation of the segmented image. The correlation feature describes the correlation of the intensity of values within the segmented image. The difference entropy feature describes the disorder of the difference between a pair of pixel intensities within the segmented image. The contrast inverse moment feature describes the inhomogeneity within a region of interest in the segmented image. The contract variance feature describes the variance of the difference between a pair of pixel intensities.

Method 300 also includes, at 340, selecting a set of shape features from the segmented image. The set of shape features may include a location feature, a size feature, a perimeter feature, an eccentricity feature, an eccentricity standard deviation, a compactness feature, a roughness feature, an elongation feature, a convexity feature, an equivalent diameter feature, a radial distance feature, an area feature, or a sphericity feature. The radial distance feature describes the radial distance from the center of mass of the tumor to a point on the defining contour of the tumor.

Method 300 also includes, at 345, selecting a set of tortuosity features from the segmented image. The set of tortuosity features may include the mean of torsion of a vessel segment, or the standard deviation of torsion of a vessel segment. The set of tortuosity features may also include the mean and standard deviation of the mean curvature of a group of vessel segments. The set of tortuosity features may also include the mean and standard deviation of the standard deviation of a vessel segment curvature and a total vessel segment length. In one embodiment, the set of tortuosity features includes at least seven tortuosity features. In another embodiment, the set of tortuosity features may include other numbers of tortuosity features, or other, different tortuosity features.

Method 300 also includes, at 350, generating a classification for the tumor based, at least in part, on the set of texture features, the set of shape features, and the set of tortuosity features. In one embodiment, the classification is made based on the set of texture features. In another embodiment, the classification is based on the set of shape features. In still another embodiment, the classification is based on a subset of the set of texture features, a subset of the set of shape features, and a subset of the set of tortuosity features. The subset of the set of texture features may be selected from the set of texture features using PCA. The subset of the set of shape features may be selected from the set of shape features using PCA. The subset of the set of tortuosity features may be selected from the set of tortuosity features using PCA. The subset of shape features, the subset of texture features, or the subset of tortuosity features may be selected to achieve a threshold level of accuracy when classifying tumors. In one embodiment, method 300 classifies the tumor as a carcinoma or a granuloma. In another embodiment, the tumor is classified as frank invasive, minimally invasive, or non-invasive. The classification may be made by a CADx system using a QDA classifier or an LDA classifier.

Method 300 also includes, at 360, providing a prognosis prediction based on the classification. For example, method 300 may, at 360, provide a probability that a patient will experience a lower five year survival rate if the tumor is classified as frank invasive. Method 300 may alternately provide a probability that a patient will experience a higher five year survival rate if the tumor is classified as non-invasive.

In one example, a method may be implemented as computer executable instructions. Thus, in one example, a computer-readable storage medium may store computer executable instructions that if executed by a machine (e.g., computer) cause the machine to perform methods described or claimed herein including method 100, method 200, and method 300. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 4:
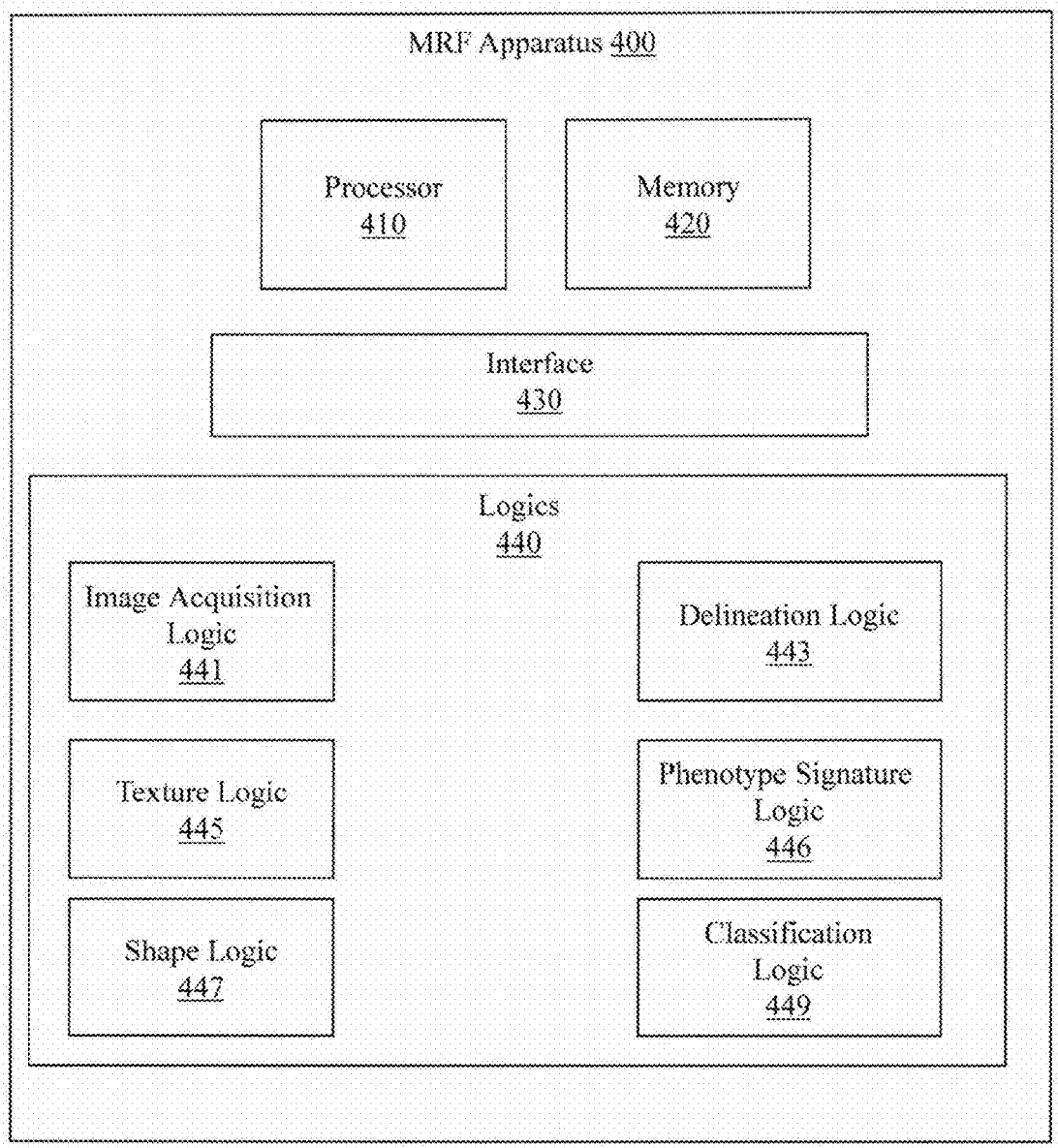
FIG. 4 illustrates an example apparatus that classifies a region of tissue in an image.

FIG. 4 illustrates an example apparatus 400 for classifying a region of tissue in an image. Apparatus 400 includes a processor 410, a memory 420, a set of logics 440, and an interface 430 that connects the processor 410, the memory 420, and the set of logics 440. The set of logics 440 includes an image acquisition logic 441, a delineation logic 443, a texture logic 445, a phenotype signature logic 446, a shape logic 447, and a classification logic 449. In one embodiment, the functionality associated with the set of logics 440 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 440 are implemented as ASICs or SOCs.

Image acquisition logic 441 acquires an image of a region of tissue. The image may be acquired from, for example, a CT apparatus. The region of tissue may be a section of tissue demonstrating cancerous pathology in a patient. The image of the region of tissue may include an image of a GGO nodule. In one embodiment, the image is a 1 mm to 5 mm thick, no-contrast chest CT image. Other imaging approaches may be used to generate and access the image accessed by image acquisition logic 441. Other image dimensions may also be used.

Delineation logic 443 automatically delineates the GGO nodule by distinguishing GGO nodule tissue within the image from the background of the image. Delineation logic 443 automatically delineates the GGO nodule using threshold based segmentation, deformable boundary models, active-appearance models, active shape models, graph based models including Markov random fields (MRF), min-max cut approaches, or other image segmentation approaches.

Texture logic 445 extracts a set of texture features from the image. The set of texture features may be extracted from the image of the delineated GGO nodule. In one embodiment, the set of texture features includes a gray-level statistical feature, a steerable Gabor feature, a Haralick feature, a Law feature, a Law-Laplacian feature, an LBP feature, inertia, correlation, difference entropy, contrast inverse moment, or contrast variance. The texture logic 445 may also select a subset of texture features from the set of texture features. Texture logic 445 may select the subset of texture features based on, at least in part, a PCA of the set of texture features.

Phenotype selection logic 446 computes a phenotypic signature of the delineated GGO nodule in the image. Phenotype selection logic 446 may compute the phenotypic signature using a Fisher criteria ranking.

Shape logic 447 extracts a set of shape features from the image. The set of shape features may include a location feature, a size feature, a perimeter feature, an eccentricity feature, an eccentricity standard deviation, a compactness feature, a roughness feature, an elongation feature, a convexity feature, an equivalent diameter feature, or a sphericity feature. Shape logic 447 also selects a subset of shape features from the set of shape features based, at least in part, on a PCA of the set of shape features.

Classification logic 449 classifies the GGO nodule tissue based, at least in part, on the set of texture features, the phenotypic signature, or the set of shape features. In one embodiment, classification logic 449 logic classifies the GGO nodule tissue as a carcinoma or a granuloma using an LDA of the subset of texture features and the subset of shape features. In another embodiment, classification logic 449 classifies the GGO nodule tissue as minimally invasive or as frank invasive using a QDA of the subset of texture features. In still another embodiment, classification logic 449 may classify the GGO nodule tissue using other analytical techniques.

In another embodiment, classification logic 449 may control a CADx system to classify the image based, at least in part, on the classification. For example, classification logic 449 may control a lung cancer CADx system to classify the image based, at least in part, on the set of texture features and set of shape features. In other embodiments, other types of CADx systems may be controlled, including CADx systems for distinguishing GGO nodules among oral cancer, prostate cancer, colon cancer, brain cancer, and other diseases where disease classification and prognosis prediction may be based on textural or shape features quantified from CT images of a GGO nodule.

In one embodiment of apparatus 400, the set of logics 440 also includes a tortuosity logic. The tortuosity logic identifies a vessel associated with the GGO nodule. The tortuosity logic identifies the centerline and a branching point of the vessel associated with the GGO nodule. The tortuosity logic computes a torsion for the segment of the vessel. The tortuosity logic also computes a curvature of a voxel of a vessel segment, where the curvature is proportional to the inverse of an osculating circle's radius. The tortuosity logic extracts a set of tortuosity features from the image. The set of tortuosity features may include the mean of torsion of a vessel segment, or the standard deviation of torsion of a vessel segment. The set of tortuosity features also may include the mean and standard deviation of the mean curvature of a group of vessel segments. The set of tortuosity features also may include the mean and standard deviation of the standard deviation of a vessel segment curvature and a total vessel segment length. The tortuosity logic also selects a subset of tortuosity features from the set of tortuosity features based, at least in part, on a PCA of the set of tortuosity features. The subset of tortuosity features may include at least three tortuosity features. In this embodiment, the classification logic 449 classifies the GGO nodule tissue based, at least in part, on the set of tortuosity features, the set of texture features, the phenotypic signature, or the set of shape features.

In one embodiment of apparatus 400, the set of logics 440 also includes a display logic. The display logic may control the CADx system to display the classification, the texture features, or the shape features on a computer monitor, a smartphone display, a tablet display, or other displays. Displaying the classification or the features may also include printing the classification or the features. The display logic may also control the CADx to display an image of the region of tissue demonstrating a GGO nodule. The image of the region of tissue demonstrating a GGO nodule may include a delineated or segmented representation of the GGO nodule. By displaying the features and the image of the GGO nodule, example apparatus provide a timely and intuitive way for a human pathologist to more accurately classify pathologies demonstrated by a patient, thus improving on conventional approaches to predicting cancer recurrence and disease progression.

Figure 5:
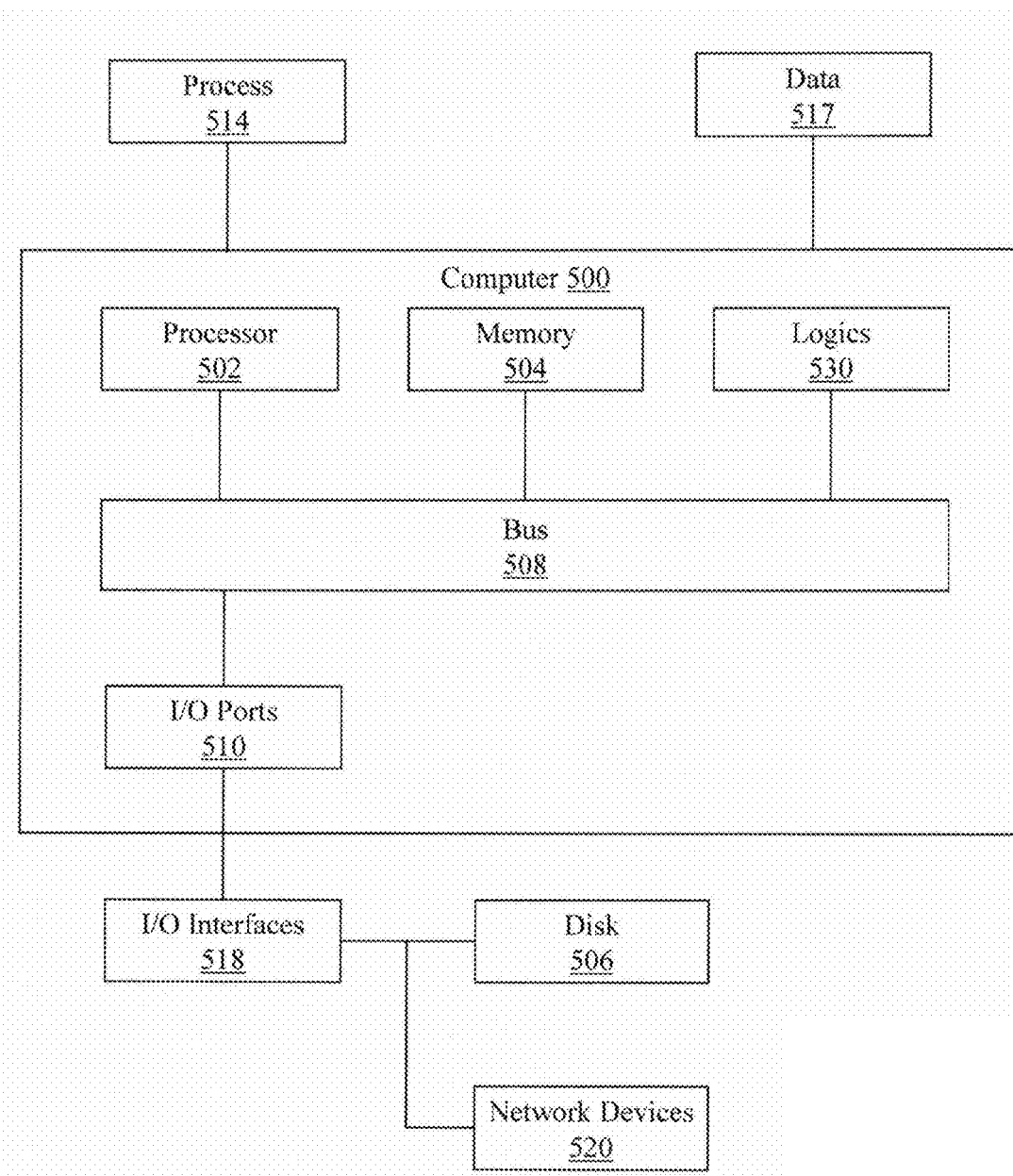
FIG. 5 illustrates an example computer in which example methods and apparatus described herein operate.

FIG. 5 illustrates an example computer 500 in which example methods illustrated herein can operate and in which example logics may be implemented. In different examples, computer 500 may be part of a CT system, may be operably connectable to a CT system, or may be part of a CADx system.

Computer 500 includes a processor 502, a memory 504, and input/output ports 510 operably connected by a bus 508. In one example, computer 500 may include a set of logics 530 that perform a method of characterizing a GGO nodule in a region of lung tissue. Thus, the set of logics 530, whether implemented in computer 500 as hardware, firmware, software, and/or a combination thereof may provide means (e.g., hardware, software) for characterizing a GGO nodule in a region of lung tissue. In different examples, the set of logics 530 may be permanently and/or removably attached to computer 500. In one embodiment, the functionality associated with the set of logics 530 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 530 are implemented as ASICs or SOCs.

Processor 502 can be a variety of various processors including dual microprocessor and other multi-processor architectures. Memory 504 can include volatile memory and/or non-volatile memory. A disk 506 may be operably connected to computer 500 via, for example, an input/output interface (e.g., card, device) 518 and an input/output port 510. Disk 506 may include, but is not limited to, devices like a magnetic disk drive, a tape drive, a Zip drive, a flash memory card, or a memory stick. Furthermore, disk 506 may include optical drives like a CD-ROM or a digital video ROM drive (DVD ROM). Memory 504 can store processes 514 or data 517, for example. Disk 506 or memory 504 can store an operating system that controls and allocates resources of computer 500.

Bus 508 can be a single internal bus interconnect architecture or other bus or mesh architectures. While a single bus is illustrated, it is to be appreciated that computer 500 may communicate with various devices, logics, and peripherals using other busses that are not illustrated (e.g., PCIE, SATA, Infiniband, 1394, USB, Ethernet).

Computer 500 may interact with input/output devices via I/O interfaces 518 and input/output ports 510. Input/output devices can include, but are not limited to, digital whole slide scanners, an optical microscope, a keyboard, a microphone, a pointing and selection device, cameras, video cards, displays, disk 506, network devices 520, or other devices. Input/output ports 510 can include but are not limited to, serial ports, parallel ports, or USB ports.

Computer 500 may operate in a network environment and thus may be connected to network devices 520 via I/O interfaces 518 or I/O ports 510. Through the network devices 520, computer 500 may interact with a network.

Through the network, computer 500 may be logically connected to remote computers. The networks with which computer 500 may interact include, but are not limited to, a local area network (LAN), a wide area network (WAN), or other networks.

References to "one embodiment", "an embodiment". "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage medium storing computer executable instructions that when executed by a computer control the computer to perform a method for characterizing a ground glass (GGO) nodule in a region of lung tissue, the method comprising:
   accessing an image of a region of lung tissue;
   delineating a GGO nodule in the image;
   extracting a set of texture features from the GGO nodule;
   selecting a subset of texture features from the set of texture features;
   extracting a set of shape features from the GGO nodule;
   selecting a subset of shape features from the set of shape features;
   generating a phenotypic signature for the nodule; and
   controlling a computer aided diagnosis (CADx) system to generate a classification of the GGO nodule in the image based, at least in part, on the subset of texture features, the subset of shape features, or the phenotypic signature.

2. The non-transitory computer-readable storage medium of claim 1, where accessing the image of the region of lung tissue includes accessing a computed tomography (CT) image of the region of lung tissue, where the CT image is a no-contrast chest CT image.

3. The non-transitory computer-readable storage medium of claim 1, the method comprising automatically delineating the GGO nodule by distinguishing GGO nodule tissue in the image from the background of the image.

4. The non-transitory computer-readable storage medium of claim 1, where the set of texture features includes at least sixty three texture features.

5. The non-transitory computer-readable storage medium of claim 1, where the set of texture features includes a gray-level statistical feature, a steerable Gabor feature, a Haralick feature, a Law feature, a Law-Laplacian feature, an LBP feature, an inertia feature, a correlation feature, a difference entropy feature, a contrast inverse moment feature, a gradient feature, or a contrast variance feature.

6. The non-transitory computer-readable storage medium of claim 1, where selecting the subset of texture features from the set of texture features includes reducing the set of texture features using principal component analysis (PCA).

7. The non-transitory computer-readable storage medium of claim 1, where the phenotypic signature is generated using Fisher criteria ranking.

8. The non-transitory computer-readable storage medium of claim 1, where the CADx system generates the classification of the image of the GGO nodule using a quadratic discriminant analysis (QDA) classifier.

9. The non-transitory computer-readable storage medium of claim 1, where the image is of a region of adenocarcinoma tissue, and where controlling the CADx system to generate the classification of the image of the GGO nodule based, at least in part, on the subset of texture features and the phenotypic signature, includes classifying the image of the GGO nodule as frank invasive adenocarcinoma or minimally invasive adenocarcinoma.

10. The non-transitory computer-readable storage medium of claim 1, where the set of shape features includes a location feature, a size feature, a width feature, a height feature, a depth feature, a radial distance feature, a perimeter feature, an eccentricity feature, an eccentricity standard deviation, a compactness feature, a roughness feature, an elongation feature, a convexity feature, an equivalent diameter feature, or a sphericity feature.

11. The non-transitory computer-readable storage medium of claim 10, where the subset of shape features includes an eccentricity feature, an eccentricity standard deviation feature, or an elongation feature.

12. The non-transitory computer-readable storage medium of claim 11, the method comprising controlling the CADx system to generate the classification of the image of the GGO nodule as a carcinoma or a granuloma based, at least in part, on the subset of texture features and the subset of shape features.

13. The non-transitory computer-readable storage medium of claim 12, the method further comprising:
  segmenting a vessel associated with the image of the GGO nodule into a plurality of vessel segments;
  computing a torsion for a vessel segment;
  computing a curvature for the vessel segment, where the curvature is proportional to the inverse of the radius of an osculating circle;
  selecting a set of tortuosity features from the image of the GGO nodule, where the set of tortuosity features includes a mean of torsion of the vessel segment, a standard deviation of torsion of the vessel segment, a mean of the mean curvature of the plurality of vessel segments, a standard deviation of the mean curvature of the plurality of vessel segments, a mean of the standard deviation of the curvature of the vessel segment, a standard deviation of the standard deviation of the curvature of the vessel segment, a total length of a vessel segment, or a total length of the plurality of vessel segments;
  selecting a subset of tortuosity features from the set of tortuosity features using a PCA of the set of tortuosity features; and
  controlling a computer aided diagnosis (CADx) system to generate a classification of the GGO nodule in the image based, at least in part, on the subset of tortuosity features, the subset of texture features, the subset of shape features, or the phenotypic signature.

14. The non-transitory computer-readable storage medium of claim 1, where the CADx system generates the classification of the image of the GGO nodule using a linear discriminant analysis (LDA) classifier or a quadratic discriminant analysis (QDA) classifier.

15. The non-transitory computer-readable storage medium of claim 14, where the LDA classifier classifies the image of the GGO nodule with an accuracy of at least 0.92 area under the curve (AUC).

16. An apparatus for classifying a region of tissue in an image, comprising:
  a processor;
  a memory;
  an input/output interface;
  a set of logics; and
  an interface to connect the processor, the memory, the input/output interface and the set of logics, where the set of logics includes:
    an image acquisition logic that acquires an image of a region of tissue demonstrating ground glass (GGO) nodule pathology;
    a delineation logic that distinguishes GGO nodule tissue in the image from the background of the image;
    a texture logic that extracts a set of texture features from the image;
    a phenotype signature logic that computes a phenotypic signature from the image;
    a shape logic that extracts a set of shape features from the image; and
    a classification logic that classifies the GGO nodule tissue based, at least in part, on the set of texture features, the phenotypic signature, or the set of shape features.

17. The apparatus of claim 16, where the set of texture features includes a gray-level statistical feature, a steerable Gabor feature, a Haralick feature, a Law feature, a Law-Laplacian feature, a gradient feature, a local binary pattern (LBP) feature, an inertia feature, a correlation feature, a difference entropy feature, a contrast inverse moment feature, or a contrast variance feature, and where the texture logic selects a subset of texture features from the set of texture features based on, at least in part, a principal component analysis (PCA) of the set of texture features.

18. The apparatus of claim 17, where the set of shape features includes a location feature, a size feature, a width feature, a height feature, a depth feature, a radial distance feature, a perimeter feature, an eccentricity feature, an eccentricity standard deviation feature, a compactness feature, a roughness feature, an elongation feature, a convexity feature, an equivalent diameter feature, or a sphericity feature, and where the shape logic selects a subset of shape features from the set of shape features based on, at least in part, a PCA of the set of shape features.

19. The apparatus of claim 18,
  where the classification logic classifies the GGO nodule tissue as a carcinoma or a granuloma using a linear discriminant analysis of the subset of texture features and the subset of shape features, or
  where the classification logic classifies the GGO nodule tissue as minimally invasive or as frank invasive using a quadratic discriminant analysis of the subset of texture features.

20. The apparatus of claim 19, the set of logics comprising a tortuosity logic that extracts a set of tortuosity features from the image, the set of tortuosity features including a mean of torsion of the vessel segment, the standard deviation of torsion of the vessel segment, a mean of the mean curvature of the plurality of vessel segments, a standard deviation of the mean curvature of the plurality of vessel segments, a mean of the standard deviation of the curvature of the vessel segment, a standard deviation of the standard deviation of the curvature of the vessel segment, a total length of a vessel segment, or a total length of the plurality of vessel segments.

21. The apparatus of claim 20, where the classification logic classifies the GGO nodule tissue based, at least in part, on the set of tortuosity features, the set of texture features, the phenotypic signature, or the set of shape features.

* * * * *